United States Patent [19]

Quay

[11] Patent Number: 4,687,659

[45] Date of Patent: Aug. 18, 1987

[54] DIAMIDE-DTPA-PARAMAGNETIC CONTRAST AGENTS FOR MR IMAGING

[75] Inventor: Steven C. Quay, Menlo Park, Calif.

[73] Assignee: Salutar, Inc., Sunnyvale, Calif.

[21] Appl. No.: 671,106

[22] Filed: Nov. 13, 1984

[51] Int. Cl.$^4$ .......................... A61K 49/00; A61B 5/05; A61B 6/00

[52] U.S. Cl. .......................................... 424/9; 128/653; 128/654; 436/173; 436/806; 556/40; 556/50; 556/63; 556/116; 556/148; 534/16

[58] Field of Search ................... 128/654, 653; 424/9; 556/40, 148, 50, 63, 116; 534/16; 436/806, 173

[56] References Cited

U.S. PATENT DOCUMENTS 3,859,337 1/1975 Herz et al. ......................... 556/148

FOREIGN PATENT DOCUMENTS 8633082 1/1983 Australia .

OTHER PUBLICATIONS

Pykett, I. L., Scientific American, May 1982, pp. 78–88.

*Primary Examiner*—Christine M. Nucker
*Assistant Examiner*—Stephen C. Wieder
*Attorney, Agent, or Firm*—Sprung Horn Kramer & Woods

[57] ABSTRACT

Homologs of Diamide-DTPA-Paramagnetic compounds (such as diamido acetyl diethylene triamine triacetic acid) provide excellent contrast agents for magnetic resonance (MR) imaging. The magnetic dipole generated by the unpaired electron within the paramagnetic (PM) atom, causes a local reduction in the bulk magnetic field of the MR system. The resulting shorting of the T1 (spin lattice) relaxation time in the local hydrogen protons within the area of interest, causes an intense "free induction signal" and a corresponding modulation in the collected scanning data. The tissue or organ of interest appears on the MR display highlighted in white. Background tissue is displayed as darker or lower intensity greys. A surface highlighted image of the small and large intestine may be obtained by venous injection of the diamide contrast agent. The contrast agent is formed by replacing two carboxylic acids on the DTPA chelator with functional amide groups. The homologs enable the Diamide-DTPA-PM contrast agents to go into solution readily, and promote organ selectivity.

27 Claims, 10 Drawing Figures

FIG.4A
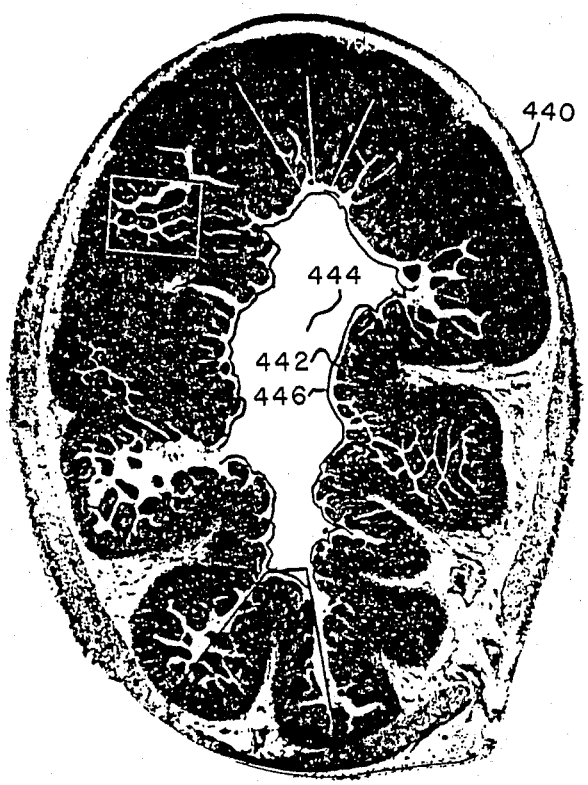
FIG.4B
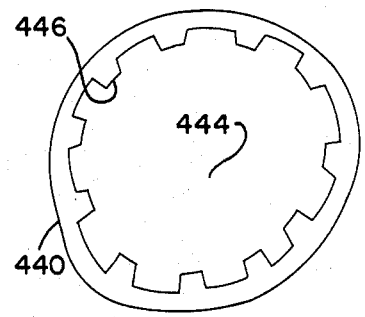
FIG.4C
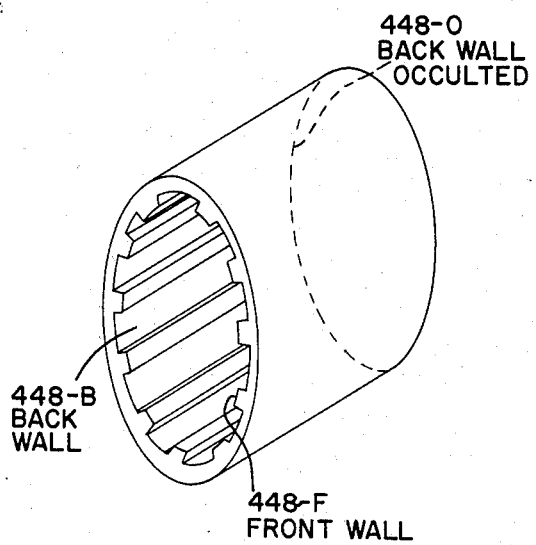
FIG.6
| STEP 1 | PROVIDING Contrast Agent Amide-DTPA-PM |
| --- | --- |
| STEP 2 | INTRODUCING Contrast Agent into Subject |
| STEP 3 | WAITING for in vivo Cooperation |
| STEP 4 | IMAGING Subject to obtain Enhanced Image |

DIAMIDE-DTPA-PARAMAGNETIC CONTRAST AGENTS FOR MR IMAGING

TECHNICAL FIELD

This invention relates to MR contrast agents, and more particularly to homologs of Amide DTPA-PM contrast agents.

BACKGROUND

Schering (German Pat. No. 3,129,906) by Gries, Rosenberg, and Weinstien teaches the incorporation of paramagnetic metals into diethylene triamine pentaacetic acid (DTPA) forming chelates useful as a contrast agent in magnetic resonance imaging. The contrast agent DTPA-(GdIII) as taught by Schering is insoluble in water and requires the addition of cations "C+" (amines such as glucamine, N-methylglucamine, etc.) as shown below: The charge balance of the Schering DTPA-Gd(III) ion is:

| Schering DTPA-Gd(III) Charge Balance | | | | | |
|---|---|---|---|---|---|
| C+ | C+ | DTPA | Gd | | |
| +1 | +1 | −5 | +3 | = | 0 |

The resulting contrast agent has three ion particles in solution for each paramagnetic atom (a particle to PM ratio of 3:1). A paramagnetic metal with a valence of two, such as Mn, would require an additional glucamine ion:

| Schering DTPA-Mn(II) Charge Balance | | | | | | |
|---|---|---|---|---|---|---|
| C+ | | C+ | C+ | DTPA | Mn | |
| +1 | + | +1 | +1 | −5 | +3 | = 0 | raising the PM to particle ratio to 4:1.

These contrast agents raise the in vivo ion concentration and disturb the local osmolarity balance. The osmolarity is normally regulated at about 300 milliosmols per liter. Increasing the osmolarity with injected ions, causes water to collect within the unbalance region which dilutes the ion concentration.

SUMMARY

It is therefore an object of this invention to provide improved amide contrast agents for MR imaging.

It is another object of this invention to provide MR amide contrast agents which have a high stability, a low toxicity and is physiologically tolerable.

It is a further object of this invention to provide amide contrast agents in pharmacological form with a low osmolarity.

It is a further object of this invention to provide amide contrast agents which are in vivo responsive.

It is a further object of this invention to provide amide contrast agents which are organ selective.

It is a further object of this invention to provide amide contrast agents which cause surface highlighting of the small and large intestine.

It is a further object of this invention to provide a method of manufacturing such amide contrast agents.

It is a further object of this invention to provide a method of using such amide contrast agents.

It is a further object of this invention to provide an MR system employing such amide contrast agents.

Briefly, these and other objects of the present invention are accomplished by providing a chemically stable physiologically tolerable contrast agent in a pharmacological state, for in vivo use during diagnostic magnetic resonance (MR) imaging. The contrast agent enhances the MR image of a subject within the MR scanning magnetic field. A paramagnetic metal ion PM(+Z) having an atomic charge of Z locally affects the MR scanning magnetic field to reduce the T1 relaxation time of local protons within the subject. The contrast agent contains a triamine chelator DTPA' securely polar bonded around the PM(+Z) ion at a plurality of coordination points, and has the form:

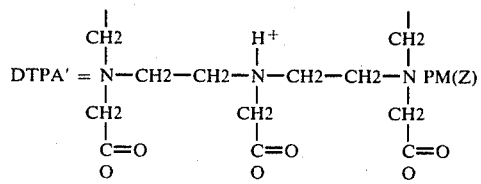

for chemically isolating the PM(+Z) ion from the in vivo environment. The contrast agent also contains a functional amide group of the form:

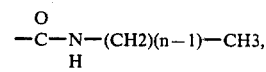

wherein "n" is an integer from 0 to 16 indicating the number of Carbon atoms in the Carbon-Hydrogen portion of each amide group. The functional amide may be a homo-diamide or a heterodiamide. The Amide-DTPA'-PM contrast agent is dispensed in a pharmaceutically acceptable vehicle means such as water. The Carbon-Hydrogen portion to the amide compound becomes associated with water of hydration which increases the paramagnetic strength of the contrast agent. The PM ion may have a valence of +3 and produce a contrast agent molecule of zero net charge. The PM ion may have a valence of +2 and require an inert cation IN having an atomic charge to produce a molecule with a zero net charge. The paramagnetic metal ion PM(+Z) is at least one element selected from the Transition Elements 24–29 or the Lanthanide Elements 57–71.

BRIEF DESCRIPTION OF THE DRAWING

Further objects and advantages of the present paramagnetic contrast agents, and the method of manufacture and use thereof, will become apparent from the following detailed description and drawing in which:

FIG. 4A is a colon shown in cross section;

FIG. 4B is a planar schematic drawing of an MR image of a colon showing surface highlighting by Diamide-DTPA-PM;

FIG. 4C is a perspective schematic drawing of an MR image of a colon showing surface highlighting by Diamide-DTPA-PM of occulted and non-occulted surfaces;

FIG. 6 is a flow chart showing a method of using the Diamide-DTPA-PM paramagnetic contrast agents.

DIAMINE-DTPA-PM CONTRAST AGENTS (FIG. 1A 1B 1C)

Figure 1A:
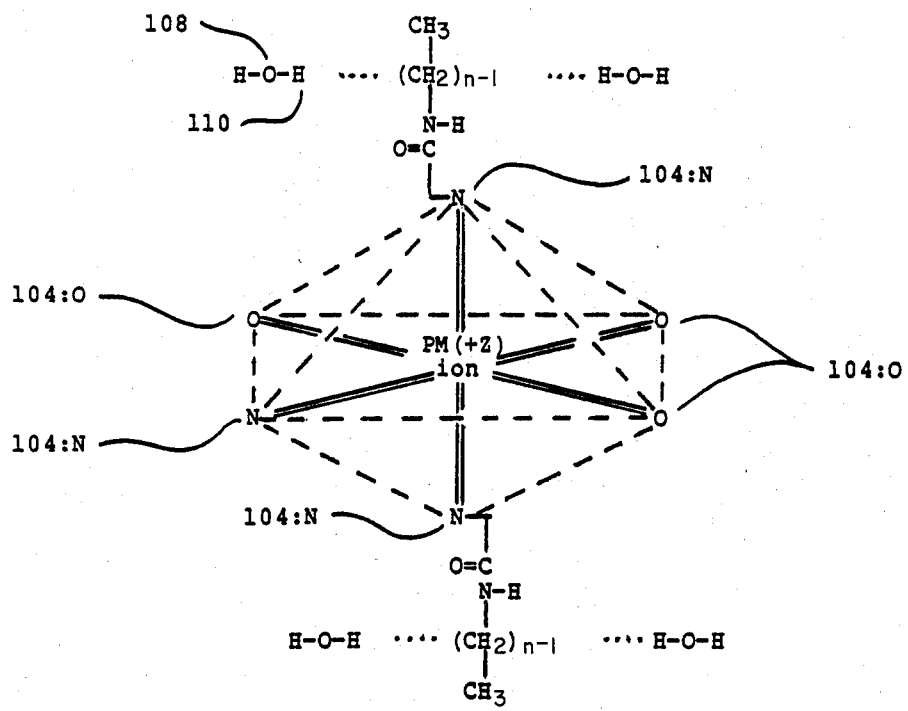
FIG. 1A is a diagram showing the chelate structure and water of hydration of a Diamide-DTPA-PM(Z) contrast agent in which Z = +3.

The present paramagnetic contrast agents are amide homologs of the DTPA-PM chelate, having the general chemical name diamido acetyl-diethylene triamine tri-acetic acid (or Diamide-DTPA). The probable physical chelation structure of Diamide-DTPA-PM is a classic octahedron (8 faces, 6 apexes) as shown in FIG. 1A. The Diamide-DTPA homologs are strong chelators having six polar bond coordination points 104 (three nitrogen points 104:N and three oxygen points 104:O) which enclose the paramagnetic ion PM(Z) on all sides.

Figure 1B:
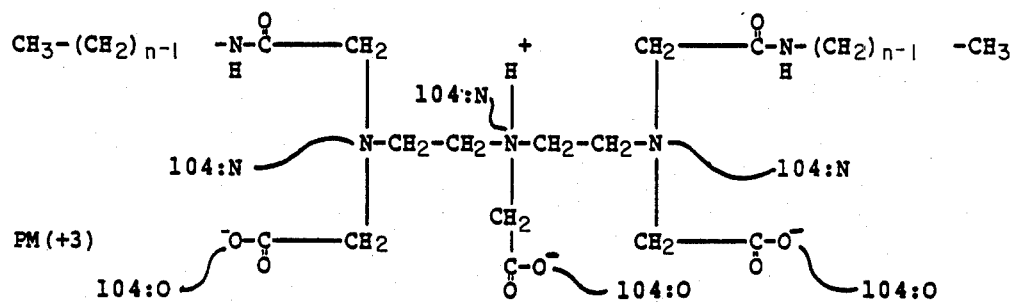
FIG. 1B is a diagram showing the chemical structure of the Diamide-DTPA-PM contrast agent of FIG. 1A.

Diamide-DTPA-PM has the general chemical structure shown in FIG. 1B. The homologs thereof have similar structures with a specific number "n" of carbons in the Carbon-Hydrogen portion of the amide group. The number of Carbons in the methylene CH2 chain between the —CONH— active group and the terminal methylene —CH3, is "n-1".

Two of the original five DTPA acetic acid groups have become amide groups "A". In general:

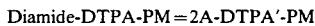
Diamide-DTPA-PM=2A-DTPA'-PM where A is a general amide group of the form:

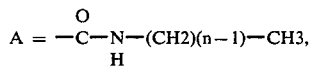
$$A = -\overset{O}{\underset{}{C}} - \underset{H}{N} - (CH2)(n-1) - CH3,$$

and DTPA' is a modification of Schering DTPA of the form:

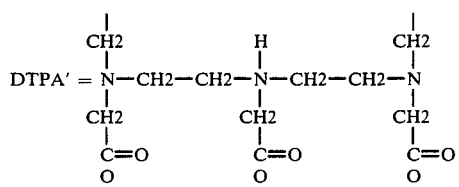

and PM is a paramagnetic metal ion. The elimination of the two acetic acid groups reduces the ion charge of the DTPA chelator from five to three.

Paramagnetic ions having a valence of $Z=+3$ as shown in FIG. 1A and 1B, produce a diamide contrast agent of the general form:

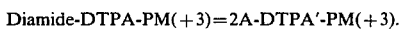
Diamide-DTPA-PM(+3)=2A-DTPA'-PM(+3).

This Type III contrast agent has a zero net charge as tabulated below:

| Diamide-DTPA-PM(+3) Charge Balance | | | | | | |
|---|---|---|---|---|---|---|
| 2A (+0) | + | DTPA' (−3) | + | PM (+3) | = | 0. |

The particle (osmolarity) to paramagnetic (molar relaxivity) ratio for Diamide-DTPA-PM(+3) type contrast agents (Z=+3) is 1:1. The Diamide-DTPA-PM(Z) contrast agents formed around plus III paramagnetic metals can be prepared in highly concentrated solutions while retaining isotonicity with body fluids. The Schering DTPA-PM(+3) has a particle to paramagnetic ratio of 3:1, and can only be made in isotonic solutions at substantially lower concentrations. Therefore, greater volumes of the Schering DTPA-PM(+3) need be injected into animals or humans to obtain the same paramagnetic effect.

Figure 1C:
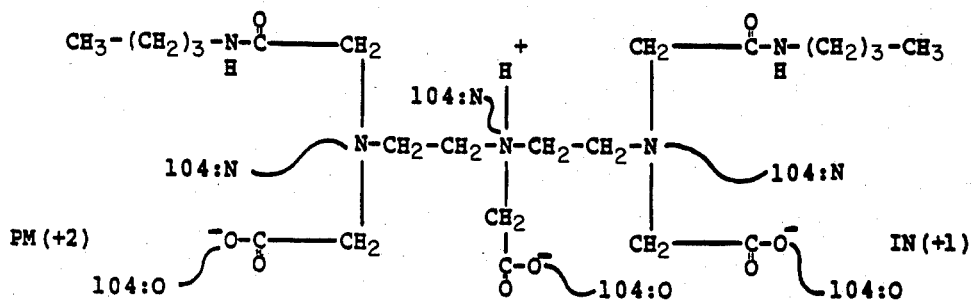
FIG. 1C is a diagram showing the chemical structure of a general Diamide-DTPA-PM(Z) contrast agent in which Z = +2.

Paramagnetic ions having a valence of $Z=2$, produce amide contrast agents of the general form:

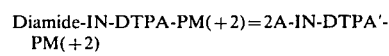
Diamide-IN-DTPA-PM(+2)=2A-IN-DTPA'-PM(+2)

where IN is a suitable inert ion, such as a simple mineral salt cation (Na+, Li+, etc.) or an organic ion such as Methyl glucamine or N-methyl glucamine, having a charge of plus one (see FIG. 1C). This Type II contrast agent also has a zero net charge as tabulated below:

| Diamide IN-DTPA-PM(+2) Charge Balance | | | | | | | | |
|---|---|---|---|---|---|---|---|---|
| 2A (+0) | + | IN (+1) | + | DTPA' (−3) | + | PM (+3) | = | 0. |

The particle to paramagnetic ratio for the IN-Diamide-DTPA-PM(+2) contrast agents is 2:1, producing a low osmolarity impact.

The above Diamide-DTPA-PM Type III and Type II contrast agents have a paramagnetic effect similar to the Schering DTPA-PM. For example, Methyl Amide DTPA-Gd(III) requires a concentration of about 3.31 mM to produce a T1 relaxation time of 67 nsec (10 MHz field strength, using an RADX). The concentration of Schering DTPA-Gd(III) required to produce a similar result is about 3.16. Methyl Amide DTPA-Gd(III) has about the same paramagnetism of Schering DTPA-Gd(III).

Possibly the water of hydration 108 (see FIG. 1A) which collects around the amide CH2 chains offers a reliable source of protons (H+) 110 for resonanting with the applied MR fields. Protons 110 have a high probability of being present within the local magnetic filed of the PM ions. These protons form a class of protons for MR imaging which is distinct from random in vivo protons. The prolonged association time of bound water 108, and the close proximity of protons 110 to the PM ion, establishes a definite and distinct T1 relaxation time which is longer than the T1 for random protons. As a result, protons 110 provided by the water of hydration appear at a higher intensity in the MR image.

Figure 2:
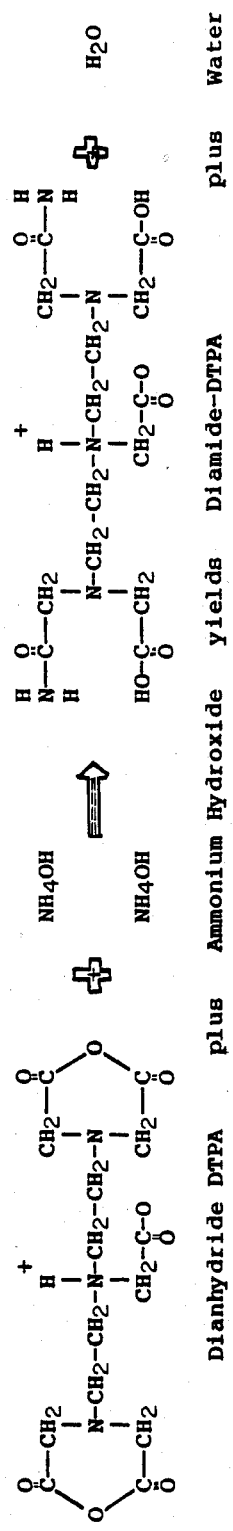
FIG. 2 is a diagram showing the anhydride ammonium hydroxide production of Dimethyl-DTPA-PM(Z) in which Z = +3.
Figure 3:
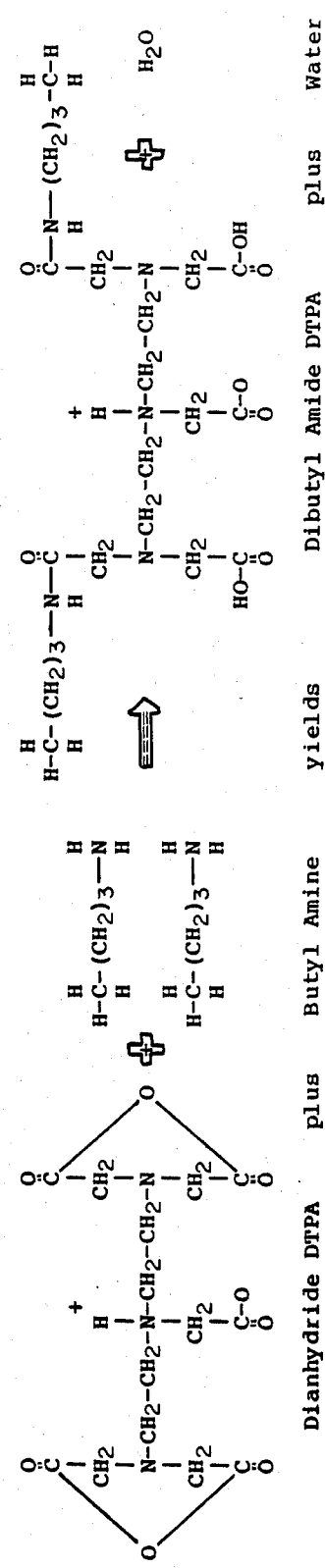
FIG. 3 is a diagram showing the anhydride butyl amine production of Dibutyl-DTPA-PM(Z) in which Z = +2.
Figure 5:
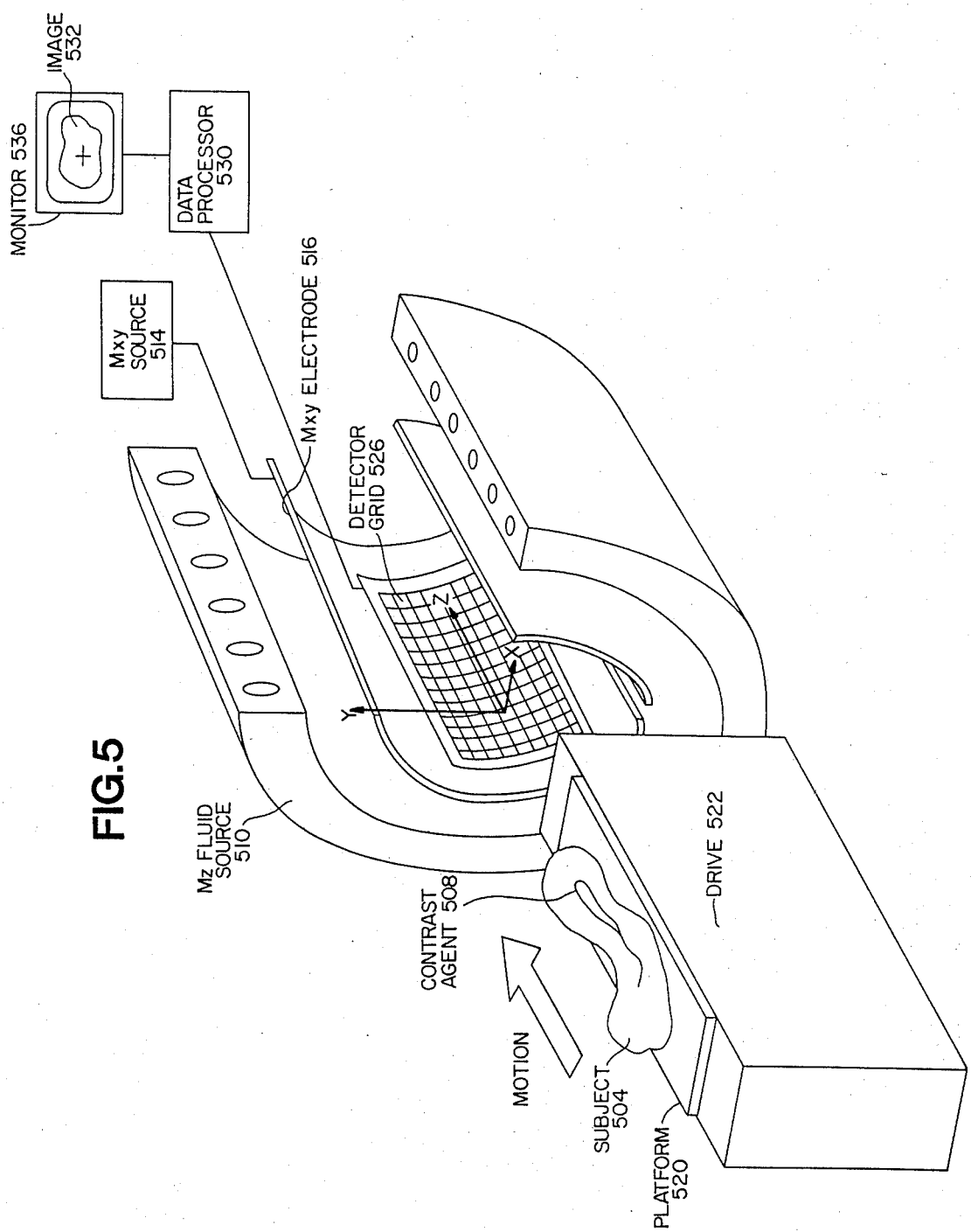
FIG. 5 is a cut-away perspective view of an MR system showing the motion platform and subject using Diamide-DTPA-PM paramagnetic contrast agents.

METHOD OF MANUFACTURE (FIGS. 2 and 3)

A general anhydride-diamide method is suitable for making each homolog of the amide family of DTPA'-PM contrast agents. In the example below the paramagnetic ion is provided by Fe(III)-(Cl)3, for chelation into dimethyl amide (n=1). However, other paramagnetic ions in other forms may be employed for chelation into other amide homologs.

Step (1)

Formation of Amide-DTPA (see FIG. 2)

Mix 1–5 grams dianhydride DTPA (obtained from Signma Chemical Co, St Louis MO.) into 50–150 mL of 5 percent (v/v) NH4-OH (ammonium hydroxide) in water. Fixed ratios of NaOH/DTPA are not required, Precise so long as excess NH4OH is provided.

Step (2)

Heat the solution for several hours (overnight) at reflux temperature, to produce the amide derivative Dimethyl-DTPA (n=1) plus water.

Higher homologs of Diamide-DTPA may be formed using the corresponding higher homolog of alkyl amines for the reactant. Chloroform may be used as the solvent for higher homologs.

Formation of the Dibutyl-DTPA (n=4) diamide homolog is shown in FIG. 3.

Step (3)

Remove the excess solvent, by vacuum rotary evaporation leaving an Diamide-DTPA crystal residue.

Step (4)

Mix the Diamide-DTPA residue in an FeCl3 water solution of stoichiometric proportions, to form Diamide-DTPA-(Fe+3) plus 3HCl.

Type II metals will require an inert cation (IN) which may be added to the solution at this point.

Step (5)

Remove the HCl
(A) by evaporation using a rotary evaporator.
(B) by neutralization using NaOH or NH4OH.
(C) by chromatograpy using a silica gel column.

Step (6)

Remove the water by vacuum-freezing to form a highly stable form of Diamide-DTPA-PM.

Step (7)

Disperse the Amide-DTPA-PM in suitable vehicle to provide a pharmacological form.

Water is a suitable vehicle for dissolving the lower homologs of Diamide-DTPA-PM (n less than 10). Higher homologs are hydrophobic and form an emulsion with water. These higher homologs have the same density as water and therefore do not settle out. The isodense character of the homologs of Diamide-DTPA-PM permits a wide range of water:homolog ratios.

ESTER FAMILY (n=0 to n=16)

The amide family of DTPA'-PM contrast agents include the homo-diamides (n=n') structures and the hetero-diamides (n not equal to n') structure.

| Name of Amide | n,n' | Properties of Interest |
|---|---|---|
| Diamide-DTPA-PM | 0,0 | Excellent |
| Methyl-DTPA-PM | 1,1 | renal and |
| Ethyl-DTPA-PM | 2,2 | blood-brain |
| Propyl-DTPA-PM | 3,3 | barrier contrast |
| Butyl-DTPA-PM | 4,4 | agent. |
| Pentyl-DTPA-PM | 5,5 | Demonstrates renal |
| Hexyl-DTPA-PM | 6,6 | and hepatobiliary |

| Name of Amide | n,n' | Properties of Interest |
|---|---|---|
| Heptyl-DTPA-PM | 7,7 | imaging. |
| Octyl-DTPA-PM | 8,8 | Also shows cardiac |
| Nonyl-DTPA-PM | 9,9 | imaging of infarctions |
| Decyl-DTPA-PM to | 10,10 16,16 | and ischemic lesions. |
| Diamide-Stearyl-DTPA-PM | 0,16 | Passes into the Cardiac system imaging. |

The hetero-diamides have one short CH2 chain (n=1 or more), and one long CH2 chain (n=16 or less). A single long hydrophobic chain, together with the charged DTPA' moiety, renders the chelate an isosteric substitute for fatty acids; and produces substantial tissue levels of the chelate in those organs which have efficient fatty acid uptake systems such as the myocardium.

ORGAN SELECTIVE (FIG. 4A 4B 4C)

Venously introduced contrast agents are immediately distributed throughout the circulatory system for imaging. Organs such as the kidney, brain, liver, and heart receive substantial blood flow; and provide selective images which are agent enhanced.

Amide-DTPA-PM has a prolonged circulation time due to its high stability. The Amide contrast agent is less affected by ensymes degradation than simple ion-DTPA chelates (Schering). In addition, the higher homologs of Amide-DTPA-PM tend to be less polar and to bind more to serum proteins, further increasing their circulation time. They tend to be extracted from circulation by the liver and excreted in the hepatobiliary system. The amide contrast agent passes through the bile duct (controlled by the ampulla of Vater) and is absorbed into the colon. The Amide contrast agents are suitable for imaging the hepatobiliary (gall bladder) system.

FIG. 4A is a cross sectional view of the colon 440. The diamide appearing along the convoluted inner surface of the colon wall 442 is slowly brushed away by the luminal content 444. The high viscosity of the contrast agent prevents it from immediately mixing with the luminal content 444. Because the washout rate is slower than the excretion rate, the agent accumulates in a film or layer 446 along the inner surface of colon 440.

The paramagnetic properties of amide enriched layer 446 establishes a shorter T1 relaxation time for the local Protons within the layer. In the resulting MR image, amide layer 446 is displayed at a higher intensity, highlighting the inner surface of the colon 440. Surface highlighted images are particularly useful in studying those disease processes involving changes in mucosal transit such as malabsorption, non-tropical sprue, ulceratine colitis, regional enteritis etc. The luminal content is not amide enriched and appears grey or dark (unenhanced) along with the background tissue.

FIG. 4B shows a schematic MR image of the colon in cross-section, and FIG. 4C shows a schematic MR image of the colon in perspective. Both simple planar views and the complex perspective views can be computer generated from the MR data. The surface amide accumulation 446 appears bright and outlines of the inner surface colon 440 unimpedded by the luminal content. This surface effect is especially noticeable in persepctive view 4C which reveals the front surface 448-F, and both the unocculted back surface 448-B and occulted back surface 448-O. The thin amide layer 446 on the front surface has a transparent characteristic which permits the occulted back surface to be viewed. The display intensity of the region of overlap between the front surface 448-F and occulted back surface 448-O is the summation of the separate intensities.

The lower homologs tend to be more polar and remain in solution longer. These homologs are kidney selective and suitable for imaging the kidney, ureter, and bladder.

The higher homologs are fatty acid analogs and are thus extracted by the heart along with the regular fatty acids. These homologs (n=7 and greater) are cardiac selective and suitable for imaging the cardiac system and cardiac related functions.

Oral introduction of the Diamide-DTPA-PM contrast agent requires a higher volume. The agent fills the luminal channel of the digestive system for providing a volume or bulk MR image.

STABLE-POWDER STATE

The stable powder state of the Diamide-DTPA-PM contrast agents have an indefinite shelf life, and is the preferred state for shipping and storage. The contrast agent in water solution (or other solvent) is packaged in small storage vials, and frozen under a vacuum. The low pressure sublimates the solvent, leaving crystals of the contrast agent. The vial is sealed to prevent entry of external contaminants, and to to preserve the internal vacuum. The resulting freeze-dried, vacuum sealed powder, is highly stable and free from environmental degradation effects.

PHARMACOLOGICAL-SOLUTION STATE

Prior to injection, the stable-powdered contrast agent may be raised to the pharmacological state by the addition of a suitable solvent such as water, serum, albumin solutions, or saline. A typical injectable composition contains about 10 mg human serum albumin (1 percent USP Parke-Davis) and from about 10 to 500 micrograms of Diamide-DTPA-PM material per milliliter of 0.01M phosphate buffer (pH 7.5) containing 0.9 percent NaCl. The pH of the aqueous solutions may range between 5–9, preferably between 6–8. The storage vial may have twin compartments containing the desired amounts of powdered Diamide-DTPA-PM and solvent for a single application. When the seal between the compartments is broken, the Diamide-DTPA-PM goes into solution at the desired concentration for immediate use. The Diamide-DTPA-PM solution mixes readily with the in vivo fluids.

PARMAGNETIC EXAMPLES

Paramagnetic material PM may be any paramagnetic element, molecule, ion or compound having a combined valance of "Z". paramagnetic material PM includes at least one of the following elements:

| Ions of Transition Elements | | | | |
|---|---|---|---|---|
| Cr(III) | 24 | (Chromium) | Co(II) | 27 | (Cobalt) |
| Mn(II) | 25 | (Manganese) | Ni(II) | 28 | (Nickel) |
| Fe(III) | 26 | (Iron) | Cu(III) | 29 | (Copper) |
| Fe(II) | 26 | (Iron) | Cu(II) | 29 | (Copper) |

| Ions of Lanthanide Elements | | | | |
|---|---|---|---|---|
| La(III) | 57 | (Lanthanum) | Gd(III) | 64 | (Gadolinium) |
| Ce(III) | 58 | (Cerium) | Tb(III) | 65 | (Terbium) |
| Pr(III) | 59 | (Praseodymium) | Dy(III) | 66 | (Dysprosium) |
| Nd(III) | 60 | (Neodymium) | Ho(III) | 67 | (Holmium) |
| Pm(III) | 61 | (Promethium) | Er(III) | 68 | (Erbium) |
| Sm(III) | 62 | (Samarium) | Tm(III) | 69 | (Thulium) |
| Eu(III) | 63 | (Europium) | Yb(III) | 70 | (Ytterbium) |
| | | | Lu(III) | 71 | (Lutetium) |

Gd has the highest paramagnetic property; but is a costly and highly toxic in the free state. Placing the Gd within the chelator produces a physiologically tolerable form of Gd; but also reduces paramagnetic effect of the Gd. The chelate structure tends to shield the paramagnetic ions and prevents close proximity to local H+ protons. Fe and Mn have a high paramagnetic property and excellent physiological tolerance. Both of these paramagnetic ions are normally present in the physiological environment.

GENERAL MR SYSTEM (FIG. 5)

Magnetic resonance (MR) imaging system 500 has two magnetic components which scan subject 504 for obtaining MR data enhanced by the presence of contrast agent 508. Bulk magnetic filed Mz from Z field source 510 causes paramagnetic particles such as local hydrogen protons within the subject to aline with the Z axis. Periodic or rotating field Mxy from XY field generator 514 extends between XY electrodes 516. The subject to be scanned is positioned on support platform 520 and moved through the magnetic fields by drive 522. Rotating field Mxy is tuned to cause resonant precession of the local protons within the tissue of interest. Each local proton precesses about the Z axis in response to a particular frequency of rotating field Mxy. When rotating field Mxy is removed, the precessing protons decay back into alinement with Mz.

The decay period of the local protons (spin lattice relaxation time T1) varies between organs and between conditions within the same organ. Tumor tissue tends to have a longer T1 than healthy tissue. The presence of the paramagnetic metal ions PM causes a shortening of the proton T1, without substantially affecting T2 (spin-spin relaxation time). The energy of precession is released forming a free induction signal. Grid detector 526 senses the decay signals which are stored and processed by data processer system 530. to form an image 532 on monitor 536. The metal ion in the contrast agent are not directly imaged by the MR system.

The imaging system if further disclosed in Scientific American, May 1982, pages 78–88, and "NMR A Primer for Medical Imaging" by Wolf and Popp Slack Book Division (ISBN 0-943432-19-7), which disclosures are hereby incorporated by reference.

METHOD OF USE (FIG. 6)

FIG. 6 shows a method of imaging subject 504 with MR system 500 employing an paramagnetic contrast agent 508.

Step (1)

Providing a physiologically tolerable contrast agent 508 in the form: 2A-DTPA-PM(+Z).

If initially in powder form, the 2A-DTPA-PM contrast agent must be dispensed into a suitable carrier vehicle.

Step (2)

Introducing the 2A-DTPA-PM contrast agent into subject 508 (preferably by intravenous injection).

Step (3)

Waiting for the amide functional groups to cooperate with the in vivo environment.

Step (4)

Imaging the subject with MR system 500 to obtain an enhanced MR image.

Comparison or subtraction imaging, requires an initial step of providing data from a prior MR imaging, and the final step of subtraction comparing the prior MR image with the current MR image. A historical base line image from the subjects file may be employed as the prior image. Alternatively, a current MR image made without the use of a contrast agent may be employed.

INDUSTRIAL APPLICABILITY

It will be apparent to those skilled in the art that the objects of this invention have been achieved as described hereinbefore by providing an improved physiologically tolerable contrast agents with a high stability, and a low toxicity. The contrast agent has a high paramagnetic effect due to the amide water of hydration, and a low osmolarity due to the amide bonding. The variability of the amide structure permits a range of vivo response and organ selection, including surface selectivity of the colon.

CONCLUSION

Clearly various changes may be made in the structure and embodiments shown herein without departing from the concept of the invention. Further, the features of the embodiments shown in the various Figures may be employed with the embodiments of the other Figures.

Therefore, the scope of the invention is to be determined by the terminology of the following claims and the legal equivalents thereof.

I claim:

1. A chemically stable physiologically tolerable contrast agent in a solid state, for use in vivo solution during diagnostic magnetic resonance (MR) imaging, to enhance the MR image the region of interest of a subject within the MR scanning magnetic field, comprising:

a composition of matter of the form:
A-DTPA-PM(+Z),
where:
A-DTPA is an ethylene triamine pentaacetic acid chelator in which at least one of the five acetic acid groups has become a functional amide group A of the form:
$A = -CONH-(CH_2)_{n-1}-CH_3$, wherein "n" is an integer up to 16, indicating the number of Carbon atoms in the Carbon-Hydrogen portion of the amide group A,
for functionally cooperating with the in vivo environment; and
PM(+Z) is a paramagnetic metal ion having an atomic charge of Z, securely chelated at a plurality of coordination points into the A-DTPA chelator to chemically isolate the PM(+Z) ion from the in vivo environment, for locally affecting the magnetic field of the MR system;

whereby the contrast agent causes a reduction in the T1 relaxation time near the region of interest within the subject.

2. The contrast agent of claim 1, wherein the composition of matter is a diamide of the form:
2A-DTPA-PM(+Z),
where:
2A-DTPA-PM(+Z) is ethylene triamine pentaacetic acid chelator in which two of the five acetic acid groups have been become a pair of functional amide groups A of the form:
$A = -CONH-(CH_2)_{n-1}-CH_3$,
wherein n is an integer up to 16, indicating the number of Carbon atoms in the Carbon-Hydrogen portion of each amide group.

3. The contrast agent of claim 2, wherein Z=+3 and 2A-DTPA-PM(+3) is a molecule having a zero net charge.

4. The contrast agent of claim 2, wherein Z=+2 and the composition of matter has the form:
2A-IN-DTPA-PM(+2),
where:
IN is an inert cation of charge +1; and
2A-IN-DTPA-PM(+2) is a molecule having a zero net charge.

5. The contrast agent of claim 1, wherein the paramagnetic metal ion PM(+Z) within the composition of matter is at least one element selected from the group consisting of:

| Ions of Transition Elements | |
| --- | --- |
| Cr(III) | Co(II) |
| Mn(II) | Ni(II) |
| Fe(III) | Cu(III) |
| Fe(II) | Cu(II) |

| Ions of Lanthanide Elements | |
| --- | --- |
| La(III) | Gd(III) |
| Ce(III) | Tb(III) |
| Pr(III) | Dy(III) |
| Nd(III) | Ho(III) |
| Pm(III) | Er(III) |
| Sm(III) | Tm(III) |
| Eu(III) | Yb(III) |
|         | Lu(III). |

6. The contrast agent of claim 1, wherein the paramagnetic metal ion PM(+Z) within the composition of matter is at least one element selected from the group consisting of:

| | |
| --- | --- |
| Cr(III) | Co(II) |
| Mn(II) | Ni(II) |
| Fe(III) | Cu(III) |
| Fe(II) | Cu(II). |
| Gd(II) | |

7. A chemically stable physiologically tolerable contrast agent in a pharmacological state, for in vivo use during diagnostic magnetic resonance (MR) imaging, to enhance the MR image of a subject within the MR scanning magnetic field, comprising:
a paramagnetic metal ion PM(+Z) having an atomic charge of Z for locally affecting the MR scanning magnetic field within the subject to reduce the T1 relaxation time thereof;

a triamine chelator DTPA' securely polar bonded around the PM(+Z) ion at a plurality of coordination points to provide a DTPA'-PM, and having the form:

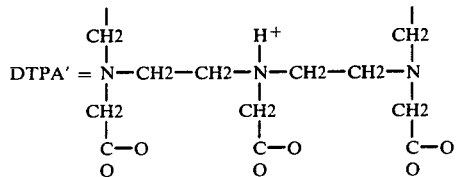

for chemically isolating the PM(+Z) ion from the in vivo environment;

functional group means formed by an amide compound of the form $CONH_2—(CH_2)_{n-1}—CH_3$, wherein "n" is an integer indicating the number of Carbon atoms in the Carbon-Hydrogen portion of the amide compound, for functionally cooperating with the in vivo environment, covalently bonded to the DTPA'-PM chelator forming an Amide-DTPA'-PM contrast agent; and a pharmaceutically acceptable vehicle means for dispersing the Amide-DTPA'-PM contrast agent.

8. The contrast agent of claim 7, wherein the functional group means comprises:

a first amide group having n1 Carbon atoms in Carbon-Hydrogen portion, and covalently bonded to the DTPA'-PM chelator; and a second amide group having n2 Carbon atoms in Carbon-Hydrogen portion, and covalently bonded to the DTPA'-PM chelator;

to form a Diamide-DTPA'-PM.

9. The contrast agent of claim 8, wherein n1 and n2 may by any whole integer from 0 to 16.

10. The contrast agent of claim 9, wherein the Diamide-DTPA'-PM is a homo-diamide in which n1=n2.

11. The contrast agent of claim 9, wherein the Diamide-DTPA'-PM is a hetero-diamide in which n1 is larger than n2.

12. The contrast agent of claim 7, wherein Z=+3 and the Amide-DTPA'-PM has a zero net charge.

13. The contrast agent of claim 7, wherein Z=+2 and the further comprises an inert cation IN having an atomic charge of +1 forming Amide-IN(+1)-DTPA'-PM(+2) with a zero net charge.

14. The contrast agent of claim 7, wherein the vehicle means is a water solution.

15. The contrast agent of claim 14, further comprising water of hydration associated with the Carbon-Hydrogen portion to the amide compound.

16. The contrast agent of claim 7, wherein the paramagnetic metal ion (PM(+Z) is at least one element selected from the group consisting of:

| Ions of Transition Elements | |
|---|---|
| Cr(III) | Co(II) |
| Mn(II) | Ni(II) |
| Fe(III) | Cu(III) |
| Fe(II) | Cu(II) |

| Ions of Lanthanide Elements | |
|---|---|
| La(III) | Gd(III) |
| Ce(III) | Tb(III) |
| Pr(III) | Dy(III) |
| Nd(III) | Ho(III) |
| Pm(III) | Er(III) |
| Sm(III) | Tm(III) |
| Eu(III) | Yb(III) |
| | Lu(III). |

17. The contrast agent of claim 7, wherein the paramagnetic metal ion PM(+Z) is at least one element selected from the group consisting of:

| | |
|---|---|
| Cr(III) | Co(II) |
| Mn(II) | Ni(II) |
| Fe(III) | Cu(III) |
| Fe(II) | Cu(II). |
| Gd(II) | |

18. The contrast agent of claim 7, wherein the paramagnetic metal ion PM(+Z) is Fe(III).

19. The contrast agent of claim 7, wherein the paramagnetic metal ion PM(+Z) is Mn(II).

20. The contrast agent of claim 7, wherein the paramagnetic metal ion PM(+Z) is Co(II).

21. The contrast agent of claim 7, wherein the paramagnetic metal ion PM(+Z) is Gd(III).

22. The method of imaging a subject with a magnetic resonance (MR) imaging system employing an paramagnetic contrast agent, comprising the steps of:

Providing a physiologically tolerable contrast agent in the form:

2A-DTPA-PM(+Z), where:

2A-DTPA is ethylene triamine pentaacetic acid chelator in which two of the five acetic acid groups have been become a pair of functional amide groups A of the form:

$A = —CONH—(CH_2)_{n-1}—CH_3$, wherein n is an integer up to 16, indicating the number of Carbon atoms in the Carbon-Hydrogen portion of each amide group, for functionally cooperating with the in vivo environment; and PM(+Z) is a paramagnetic metal ion having an atomic charge of +Z, securely chelated at a plurality of coordination points into the 2A-DTPA chelator to chemically isolate the PM(+Z) ion from the in vivo environment, for locally affecting the magnetic field of the MR system;

introducing the 2A-DTPA-PM contrast agent into the subject;

Waiting for the amide functional groups to cooperate with the in vivo environment; and Imaging the region of interest within a subject with the MR system to obtain a contrast agent enhanced MR image.

23. The method of imaging a subject as specified in claim 22, wherein the contrast agent is introduced by intravenous injection.

24. The method of imaging a subject as specified in claim 22, further comprising the initial step of dispersing the 2A-DTPA-PM contrast agent into a suitable carrier vehicle.

25. The method of imaging a subject as specified in claim 22, further comprising:
the initial step of providing data from a prior MR imaging: and
the final step of subtraction comparing the prior MR image with the current MR image.

26. The method of imaging a subject as specified in claim 22, wherein the region of interest is the gall bladder and the colon.

27. The method of imaging a subject as specified in claim 26, wherein the resulting image is a perspective image of the surface of the colon.

* * * * *

UNITED STATES PATENT AND TRADEMARK OFFICE

CERTIFICATE EXTENDING PATENT TERM
UNDER 35 U.S.C. § 156

PATENT NO.: 4,687,659

DATED: August 18, 1987

INVENTOR: Steven C. Quay

PATENT OWNER: Nycomed Salutar, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

873 DAYS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
   Commissioner of Patents and Trademarks